(12) United States Patent
Martinez-Arraras (10) Patent No.: US 9,095,684 B2
(45) Date of Patent: Aug. 4, 2015

(54) BIDIRECTIONAL INTRODUCER CATHETER (76) Inventor: Joaquin Martinez-Arraras, Amarillo, TX (US)

(*) Notice: Subject to any disclaimer, the term of this patent is extended or adjusted under 35 U.S.C. 154(b) by 715 days.

(21) Appl. No.: 12/658,582

(22) Filed: Feb. 9, 2010

(65) Prior Publication Data

US 2011/0196233 A1    Aug. 11, 2011

(51) Int. Cl.
*A61M 25/00* (2006.01)
*A61M 25/06* (2006.01)
*A61B 17/34* (2006.01)
*A61M 29/00* (2006.01)
*A61M 25/09* (2006.01)

(52) U.S. Cl.
CPC ........ *A61M 25/0662* (2013.01); *A61B 17/3415* (2013.01); *A61M 25/0054* (2013.01); *A61M 29/00* (2013.01); *A61M 2025/09175* (2013.01)

(58) Field of Classification Search
CPC .......... A61B 17/3415; A61M 25/0053; A61M 25/0054; A61M 29/00; A61M 2029/025; A61M 25/00662; A61M 25/09; A61M 2025/09175; A61M 25/0041
USPC ......... 600/435; 606/108; 604/164.1, 171, 525
See application file for complete search history.

(56) References Cited

U.S. PATENT DOCUMENTS

| | | | | | |
|---|---|---|---|---|---|
| 5,492,530 | A | * | 2/1996 | Fischell et al. | 604/510 |
| 6,059,738 | A | * | 5/2000 | Stoltze et al. | 600/585 |
| 6,199,262 | B1 | * | 3/2001 | Martin | 29/525.15 |
| 2001/0021840 | A1 | * | 9/2001 | Suresh et al. | 604/525 |
| 2003/0144657 | A1 | * | 7/2003 | Bowe et al. | 606/41 |
| 2004/0243102 | A1 | * | 12/2004 | Berg et al. | 604/525 |

* cited by examiner

*Primary Examiner* — Katherine Rodjom
(74) *Attorney, Agent, or Firm* — John Bruckner PC (57) ABSTRACT

A bidirectional introducer includes a dilator having a distal end portion that includes at first section having a distal first section end, a second softer section having a proximal second section end and a distal second section end and a third reinforced section having a proximal third section end, wherein a) the distal first section end is coupled to the proximal second section end and the distal second section end is coupled to the proximal third section end and b) i) at least a portion of the first section is characterized by a first rigidity and at least a portion of the second softer section is characterized by a second rigidity that is lower than the first rigidity, and ii) at least a portion of the third reinforced section is characterized by a third rigidity that is higher than both the first rigidity and the second rigidity.

12 Claims, 12 Drawing Sheets

BIDIRECTIONAL INTRODUCER CATHETER

BACKGROUND INFORMATION

1. Field of the Invention

Embodiments of the invention relate generally to the field of cardio/vascular intervention, especially angiograpy. More particularly, an embodiment of the invention relates to a bidirectional introducer catheter with an antegrade/retrograde access sheath to allow both catheter directions through a single arteriotomy. In more detail, the bidirectional introducer catheter is enabled by an antegrae/retrograde access sheath that includes dilator that includes a distal end with softer section and one or more reinforced arch(es).

2. Discussion of the Related Art

Figure 1:
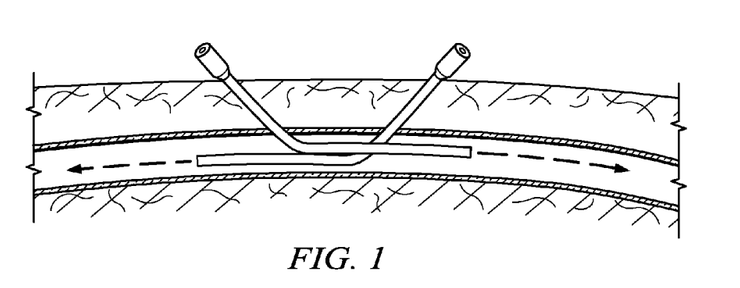
FIG. 1 is a view of two catheter sheaths, one positioned for retrograde access and the other positioned for antegrade access.
Figure 2:
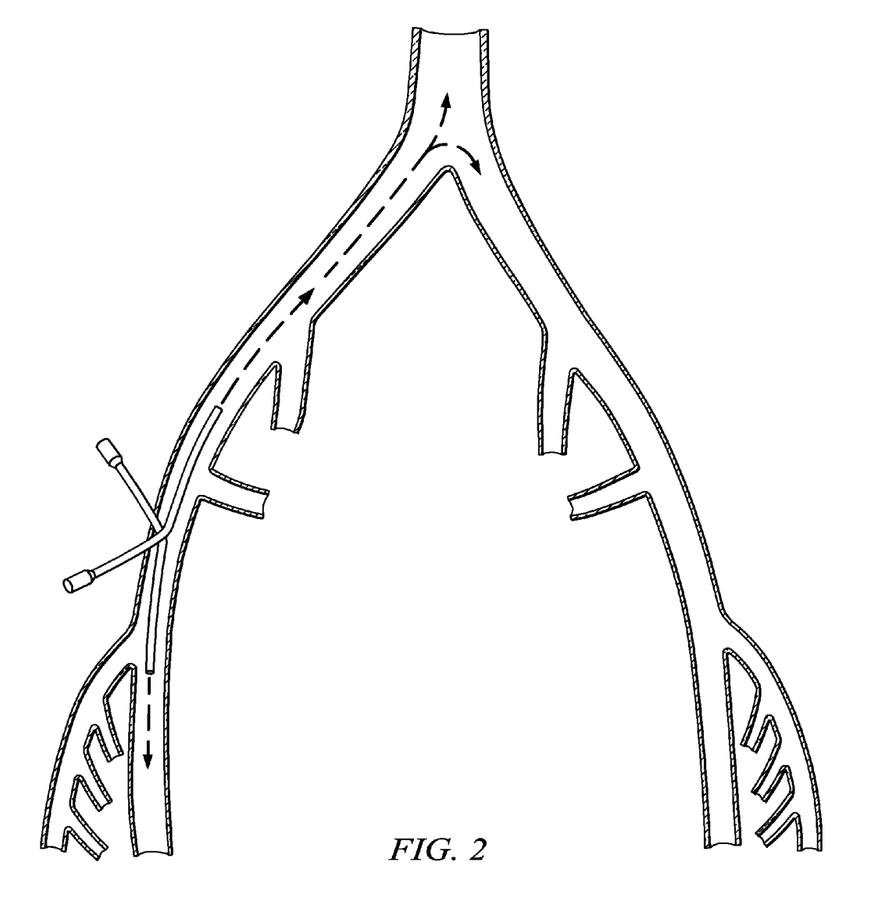
FIG. 2 is a larger scale view of two catheter sheaths, again one positioned for retrograde access and the other positioned for antegrade access.

Referring to FIGS. 1-2, retrograde access limits access to distal vascular beds due to length of trajectory; and increased catheter friction due to the sharp angulation of the aorto Iliac bifrication. Also, retrograde access limits possible imaging of the ipsilateral limb. Reversal of access direction is very difficult or impossible with current technique.

Figure 3:
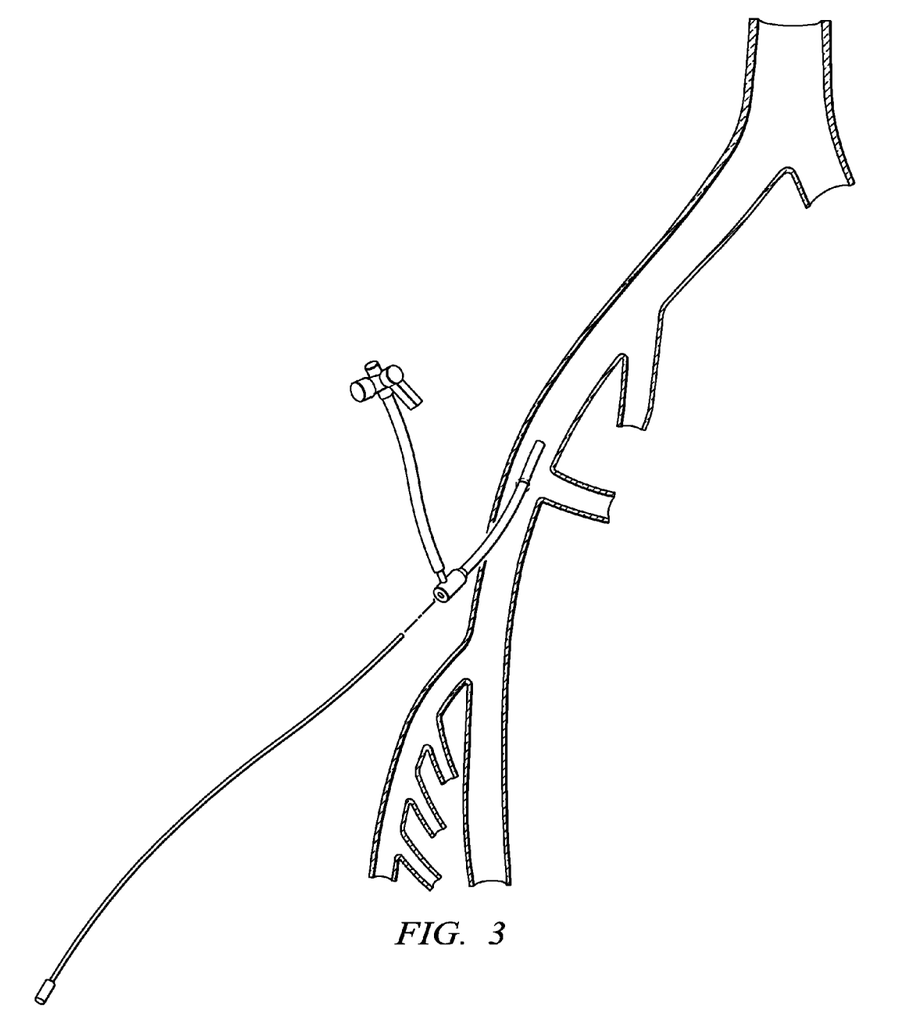
FIG. 3 is a view of a catheter sheath positioned for antegrade access and a dilator ready to be introduced into the sheath.
Figure 4:
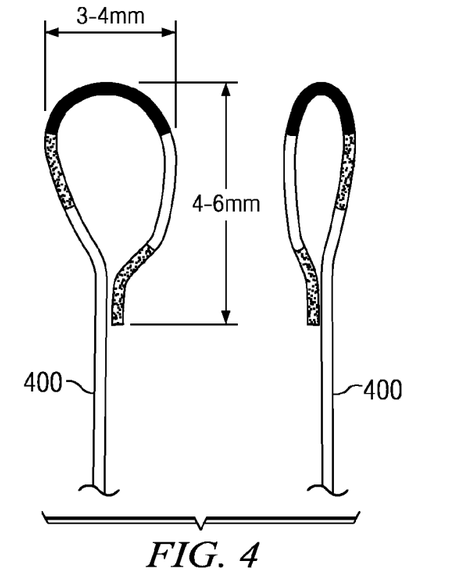
FIGS. 4-7 are four set views of four bidirectional introducer dilators (each member of each of set shown axially rotated 90 degrees to illustrate the three dimensional compound curve shape of each of the four dilators.
Figure 5:
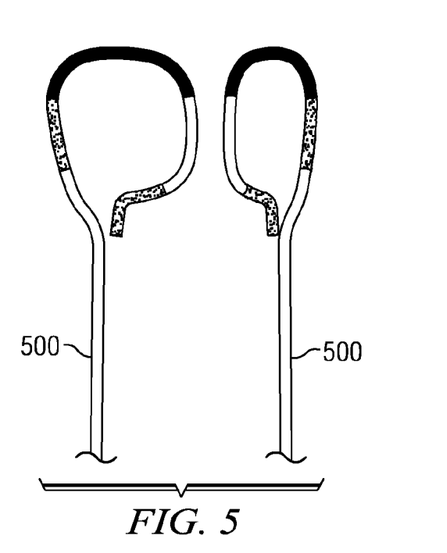
Figure 6:
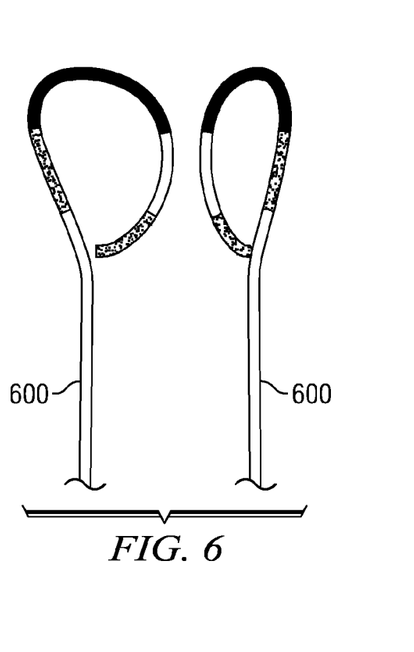
Figure 7:
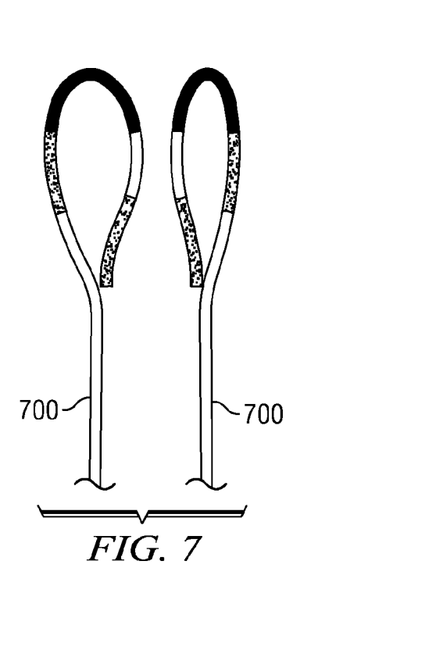

Referring to FIGS. 1-3, antegrade access has these same limitations and, in addition, is technically more difficult due to anatomical considerations, especially in obese patients. Many interventionalists are daunted by this due to lack of training.

What are needed are more effective and efficient devices for access. What are also needed are devices for reversible or bidirectional introduction of catheters.

SUMMARY OF THE INVENTION

There is a need for the following embodiments of the invention. Of course, the invention is not limited to these embodiments.

According to an embodiment of the invention, a bidirectional introducer comprises a catheter including: a sheath; and a dilator located within and substantially coaxially with the sheath, the dilator having a distal end portion that includes at first section having a proximal first section end and a distal first section end, a second softer section having a proximal second section end and a distal second section end and a third reinforced section having a proximal third section end and a distal third section end, wherein a) the distal first section end is coupled to the proximal second section end and the distal second section end is coupled to the proximal third section end and b) i) at least a portion of the first section is characterized by a first rigidity and at least a portion of the second softer section is characterized by a second rigidity that is lower than the first rigidity and ii) at least a portion of the third reinforced section is characterized by a third rigidity that is higher than both the first rigidity and the second rigidity, wherein the distal end portion includes a fourth section having a proximal fourth section end and a distal fourth section end, wherein a) the distal third section end is coupled to the proximal fourth section end and b) at least a portion of the fourth section is characterized by a fourth rigidity that is lower than the third rigidity and higher than the second rigidity, and further comprising a guide wire located within and substantially coaxially with the dilator, wherein the guide wire can be moved relative to the dilator to increase a radius of curvature characterized by the distal end portion, wherein the distal end portion includes a fifth softer section having a proximal fifth section end and a distal fifth section end, wherein a) the distal fourth section end is coupled to the proximal fifth section end and b) at least a portion of the fifth softer section is characterized by a fifth rigidity that is lower than the first rigidity.

According to another embodiment of the invention, a method of using a bidirectional introducer catheter comprises inserting a sheath, dilator and guide wire into a mammal; partially withdrawing the guide wire with regard to the dilator to reversibly deform the dilator, partially withdrawing the dilator to reposition the dilator with regard to the sheath; at least partially withdrawing the sheath; rotationally swinging the sheath into a reversed position; reinserting the guide wire to reform the dilator; and reinserting the sheath.

These, and other, embodiments of the invention will be better appreciated and understood when considered in conjunction with the following description and the accompanying drawings. It should be understood, however, that the following description, while indicating various embodiments of the invention and numerous specific details thereof, is given for the purpose of illustration and does not imply limitation. Many substitutions, modifications, additions and/or rearrangements may be made within the scope of an embodiment of the invention without departing from the spirit thereof, and embodiments of the invention include all such substitutions, modifications, additions and/or rearrangements.

BRIEF DESCRIPTION OF THE DRAWINGS

The drawings accompanying and forming part of this specification are included to depict certain embodiments of the invention. A clearer concept of embodiments of the invention, and of components combinable with embodiments of the invention, and operation of systems provided with embodiments of the invention, will be readily apparent by referring to the exemplary, and therefore nonlimiting, embodiments illustrated in the drawings (wherein identical reference numerals (if they occur in more than one view) designate the same elements). Embodiments of the invention may be better understood by reference to one or more of these drawings in combination with the following description presented herein. It should be noted that the features illustrated in the drawings are not necessarily drawn to scale.

DESCRIPTION OF PREFERRED EMBODIMENTS

Embodiments of the invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the embodiments of the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

The ability to reverse catheter direction during intervention will optimize angiograpy. Also, the ability to reverse catheter direction during intervention would make multi-vessel intervention feasible, which would result in very significant equipment savings and patient convenience.

Referring to FIGS. 4-7, an appropriately shaped "shepherds crook" sheath dilator with reinforcement in its arch, and appropriately sized to navigate through Iliac arteries, will allow for reversal of direction in a large percentage of patients, with minimal additional training for the interventionalist and at very little additional cost. It is important to appreciate that FIGS. 4-7 are four set views of four different bidirectional introducer dilators 400, 500, 600, 700 (each member of each of set shown axially rotated 90 degrees to illustrate the three dimensional compound curve shape of each of the four dilators). In more detail, and still referring to FIGS. 4-7, The lightly shaded areas are softer, for instance, rubberized or siliconized. The darker shaded areas are reinforced for shape retention and support.

Shape and size(s) of the tip(s) may need to be tested prior to arriving at a preferred shape for a generic, subgeneric and/or specific intervention and/or patient. While not being limited to any particular performance indicator, preferred embodiments of the invention can be identified one at a time by testing that the catheter preferably will straighten on a standard 0.035" guidewire. Among the other ways in which to seek guidance toward the next preferred embodiment, this can be based on the presence of initial shape retention preferably sufficient to allow for traversing the Iliac arteries in its conformation and in an atraumatic manner. Among the other ways in which to seek guidance toward the next preferred embodiment, this can be based on the presence of enough torque control preferably being present to allow for some directional maneuvers when in the common femoral artery to be able to sub-select the superficial femoral artery.

An embodiment of the invention can also be included in a kit-of-parts. The kit-of-parts can include some, or all, of the components that an embodiment of the invention includes. The kit-of-parts can be an in-the-field retrofit kit-of-parts to improve existing systems that are capable of incorporating an embodiment of the invention. The kit-of-parts can include software, firmware and/or hardware for carrying out an embodiment of the invention. The kit-of-parts can also contain instructions for practicing an embodiment of the invention. Unless otherwise specified, the components and/or instructions of the kit-of-parts can be the same as those used in an embodiment of the invention.

The particular manufacturing process used for fabrication of the bidirectional introducer catheter dilator should be inexpensive and reproducible. Conveniently, the fabrication of an embodiment of the invention can be carried out by using any joining method for coupling the sections of differing rigidity. It is preferred that the process be capable of producing a finished article of manufacture having resilient and predicable rigidity and also importantly elastic properties. For the manufacturing operation, it is an advantage to employ a glue based end-to-end joining technique.

However, the particular manufacturing process used for fabricating the bidirectional introducer catheter dilator is not essential to an embodiment of the invention as long as it provides the described functionality. Normally those who make or use an embodiment of the invention will select the manufacturing process based upon tooling and energy requirements, the expected application requirements of the final product, and the demands of the overall manufacturing process. For instance, the different sections could be coupled with snap-fit technology, infrared welding, injection molding of segregated charge batch or any other suitable joining technique.

The particular material used for the bidirectional introducer catheter dilator should be non-toxic and biocompatible. Conveniently, the dilator of an embodiment the invention can be made of any multipolymer material. It is preferred that the material be capable of providing a multi-interventional service life. For the manufacturing operation, it is an advantage to employ a copolymer material.

However, the particular material selected for the bidirectional introducer catheter dilator is not essential to an embodiment of the invention, as long as it provides the described function. Normally, those who make or use an embodiment of the invention will select the best commercially available material based upon the economics of cost and availability, the expected application requirements of the final product, and the demands of the overall manufacturing process. For instance, the material might be a thermoplastic copolymer that is extrusion processed with a variable size die to produce sections of variable outer diameter or variable fluting geometry, thereby yielding a finished dilator with sections of differing rigidity, even though they be composed of the same material.

The disclosed embodiments show a multi-section (compound) arcuate (that might be compared to a shepard's crook as the structure for performing the function of reversal, but the structure for performing reversal deformation can be any other structure capable of performing the function of reversal, including, by way of example a spiral shape, a screw shape, a quadrahedral shape or other three dimensional polygon.

EXAMPLES

Specific embodiments of the invention will now be further described by the following, nonlimiting examples which will serve to illustrate in some detail various features. The following examples are included to facilitate an understanding of ways in which an embodiment of the invention may be practiced. It should be appreciated that the examples which follow represent embodiments discovered to function well in the practice of the invention, and thus can be considered to constitute preferred mode(s) for the practice of the embodiments of the invention. However, it should be appreciated that many changes can be made in the exemplary embodiments which are disclosed while still obtaining like or similar result without departing from the spirit and scope of an embodiment of the invention. Accordingly, the examples should not be construed as limiting the scope of the invention.

Example 1

Figure 8:
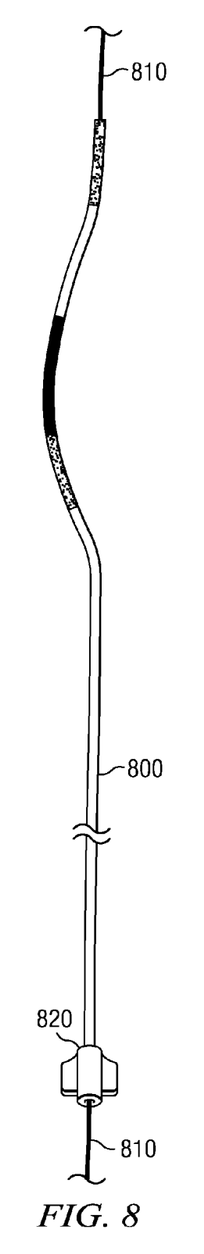
FIGS. 8-10 are three views of a bidirectional introducer dilator with a guide wire located in the dilator positioned at three stages of withdrawal.
Figures 9, 10:
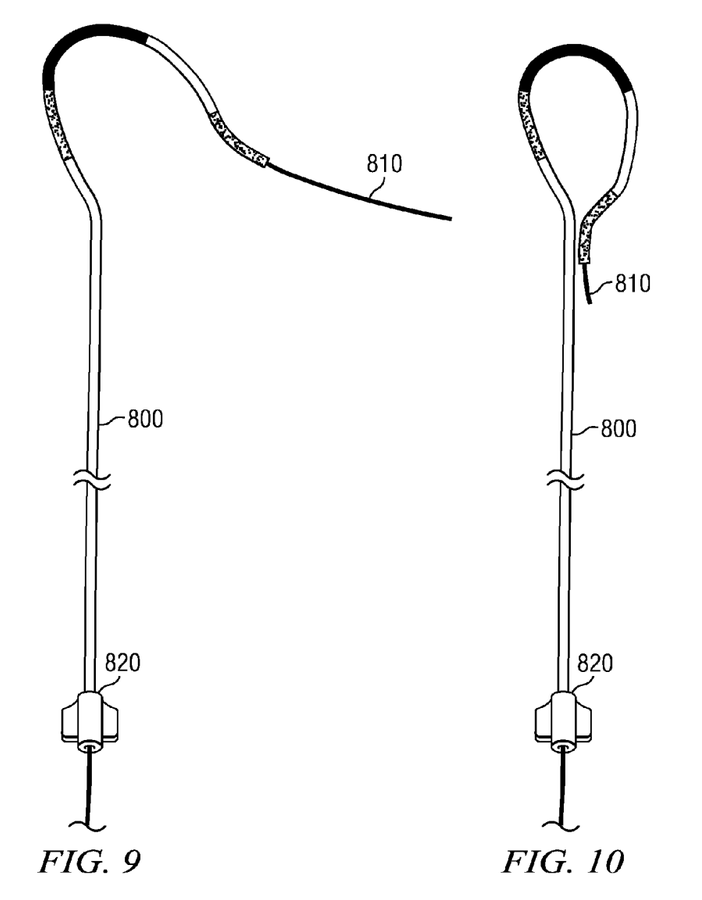

Referring to FIGS. 8-10, a single bidirectional introducer catheter 800 is shown. FIG. 8 shows the guide wire fully inserted into the dilator 820. FIG. 9 shows the guide wire 810 partially inserted into the dilator 820. FIG. 10 shows the guide wire 810 largely retracted into the dilator 820. Of course, the invention is not limited to the particular components or positions depicted in FIGS. 8-10.

Example 2

Figure 11:
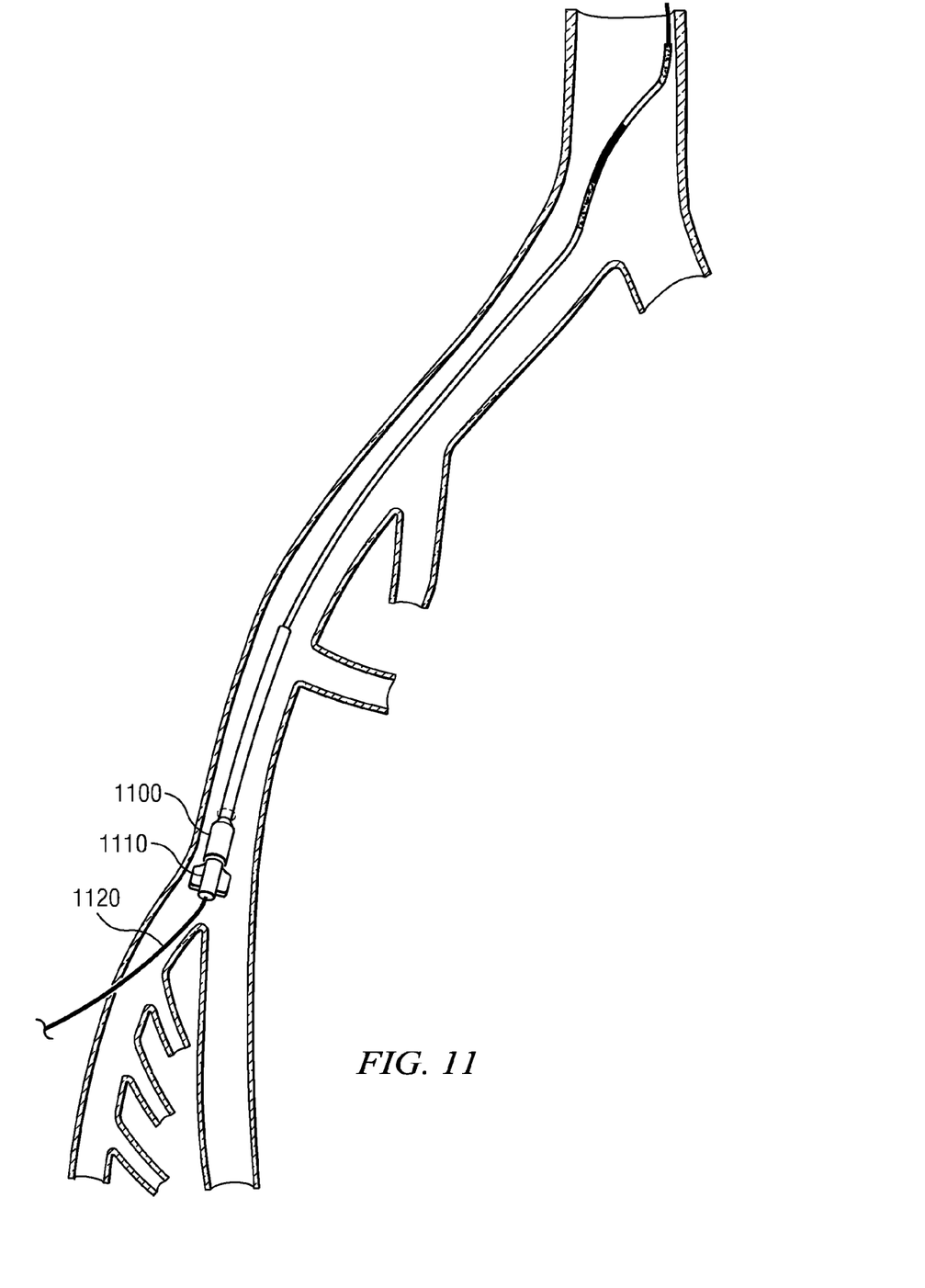
FIG. 11 is a view of a bidirectional introducer positioned for antegrade access showing the sheath, dilator and guide wire.
Figure 12:
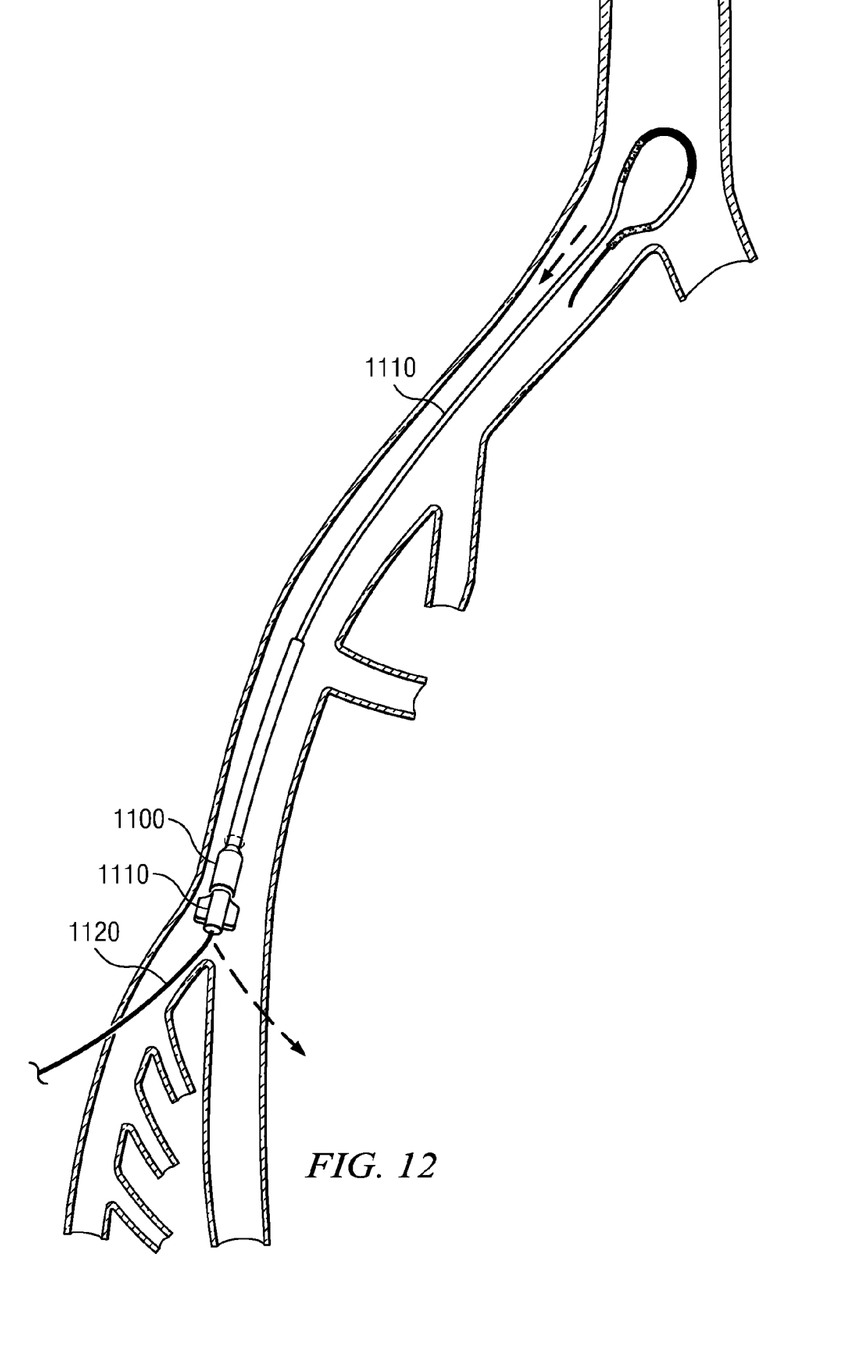
FIG. 12 is a view of the bidirectional introducer about to begin being repositioned for retrograde access showing the sheath, dilator and guide wire now partially withdrawn with regard to the sheath and dilator.
Figure 13:
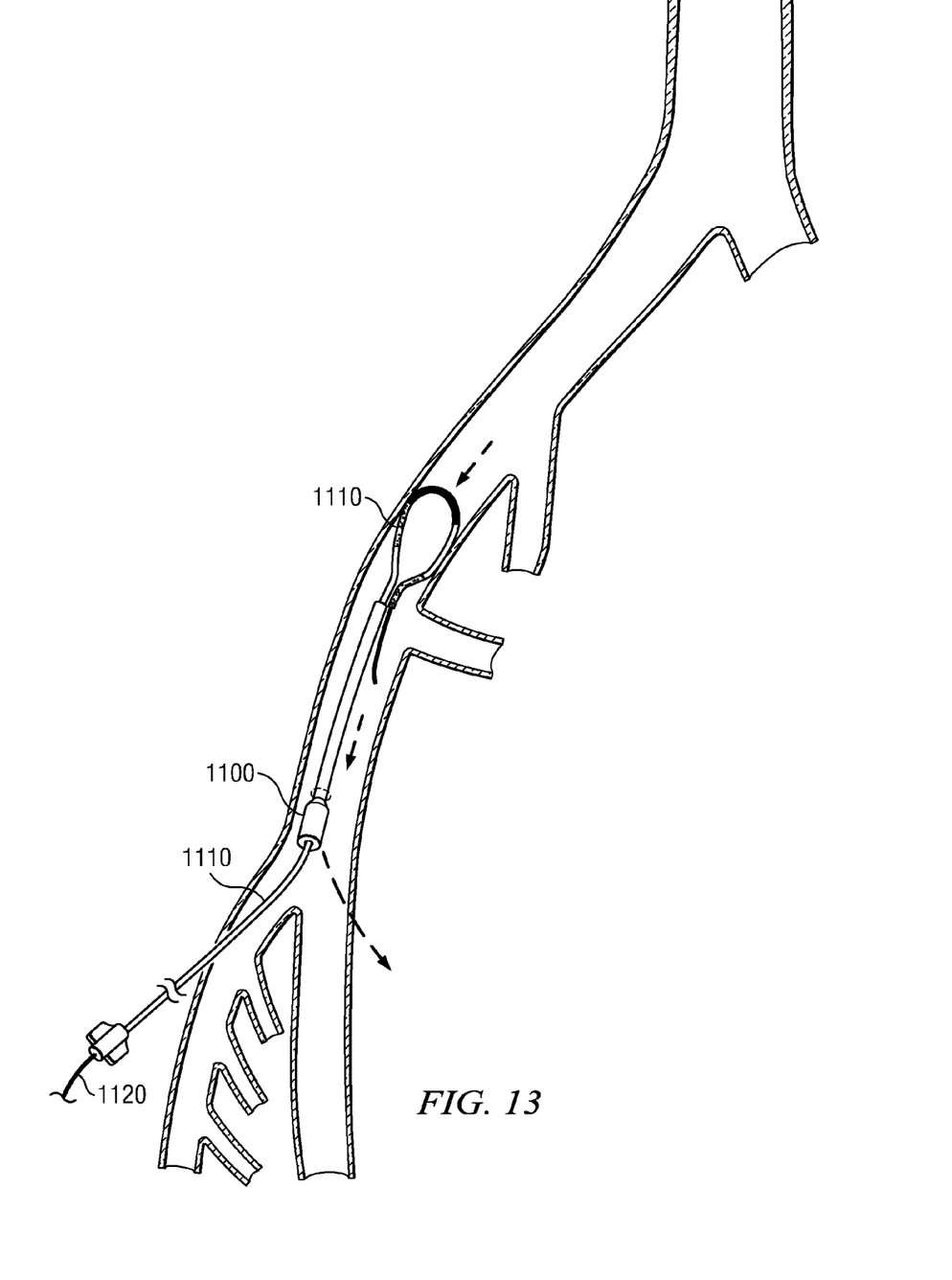
FIG. 13 is a view of the bidirectional introducer being repositioned for retrograde access showing the sheath, dilator now partially withdrawn with regard to the sheath, and, guide wire again partially withdrawn.
Figure 14:
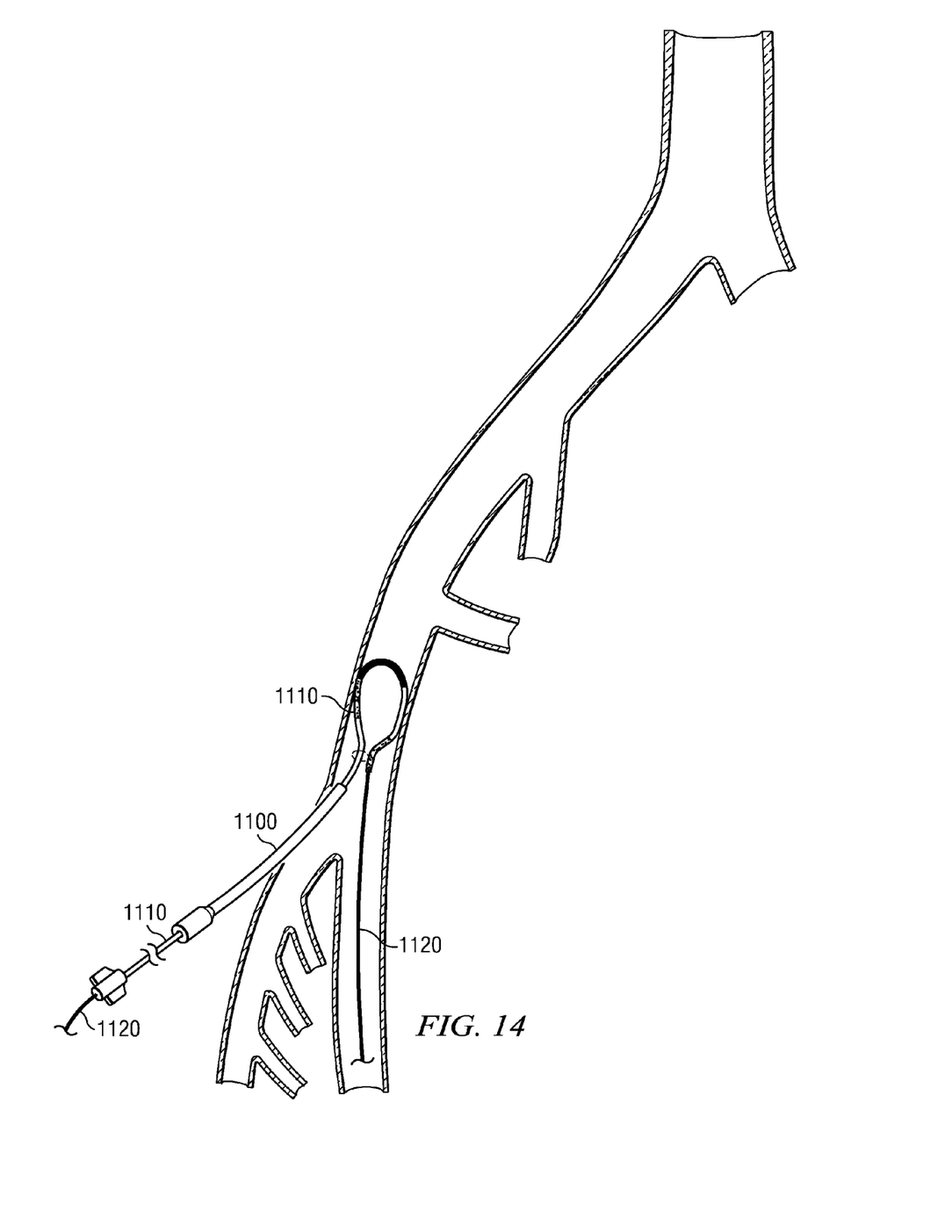
FIG. 14 is a view of the bidirectional introducer being repositioned for retrograde access showing the sheath now partially withdrawn, dilator again partially withdrawn, and, guide wire now re-extended.
Figure 15:
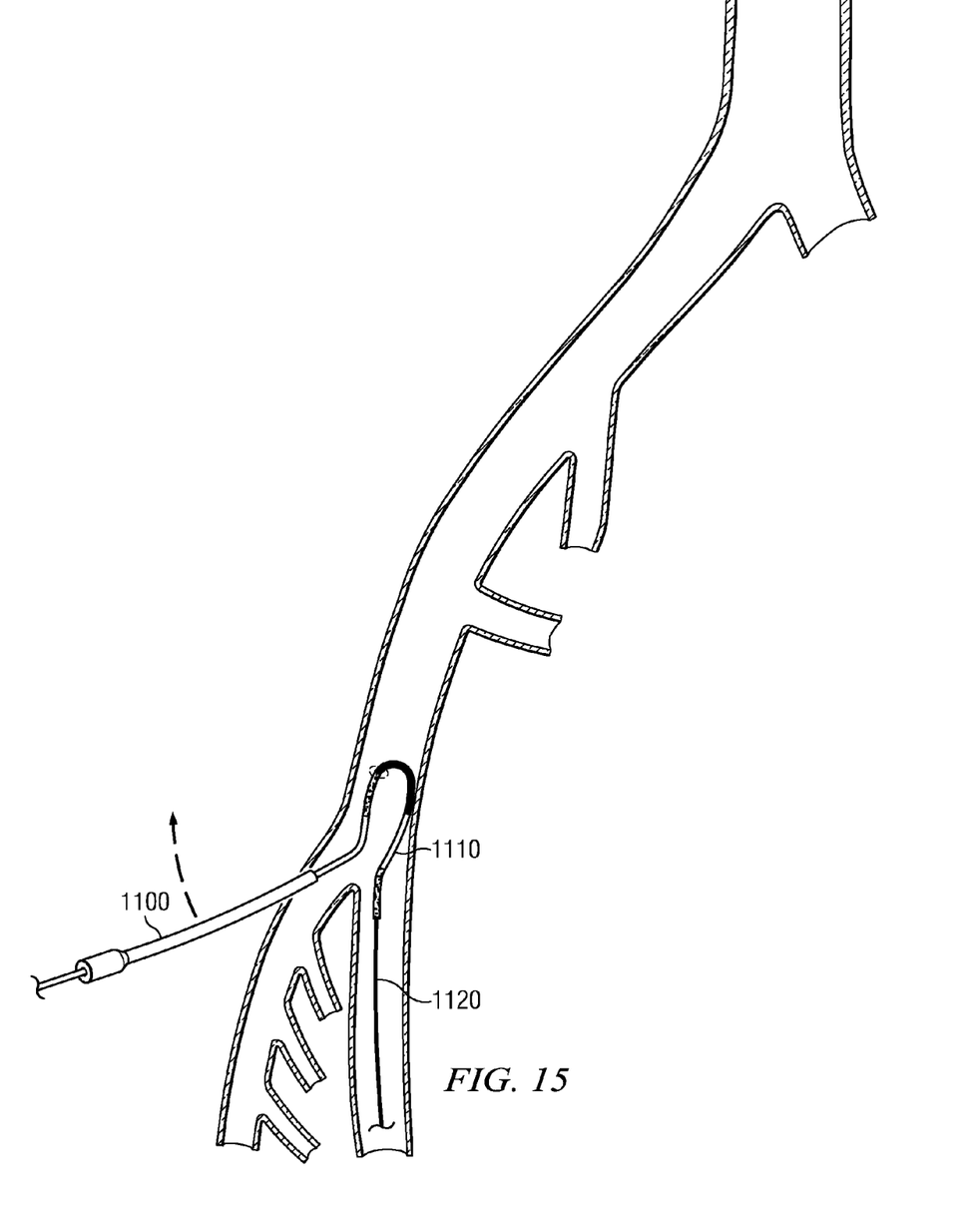
FIG. 15 is a view of the bidirectional introducer being repositioned for retrograde access showing the sheath now being swung toward reversed position, dilator again partially withdrawn, and, guide wire re-extended.
Figure 16:
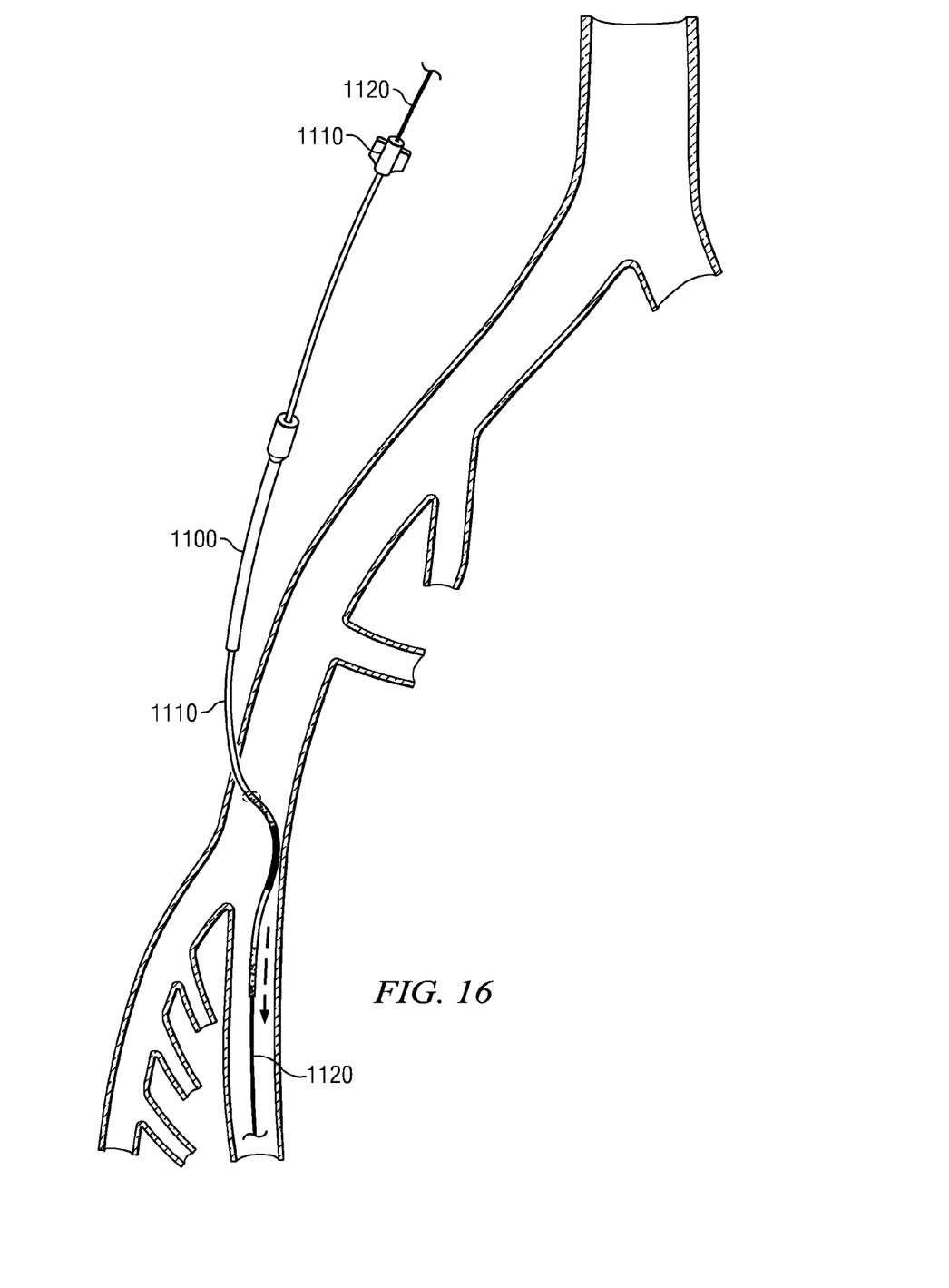
FIG. 16 is a view of the bidirectional introducer being repositioned for retrograde access showing the sheath further swung toward reversed position, dilator now being reinserted, and, guide wire re-extended.
Figure 17:
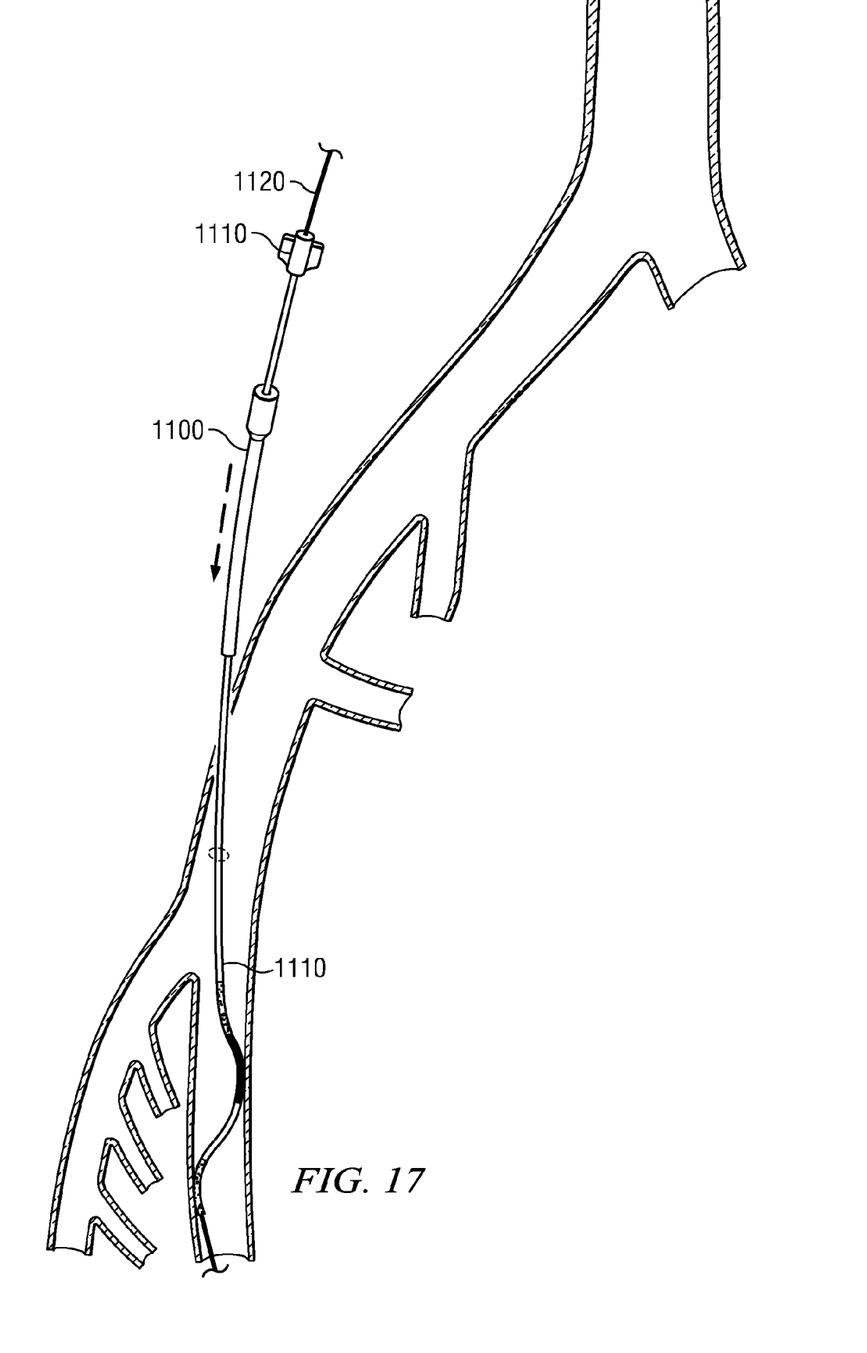
FIG. 17 is a view of the bidirectional introducer being further repositioned for retrograde access showing the sheath now being reinserted, dilator still partially reinserted, and, guide wire re-extended.
Figure 18:
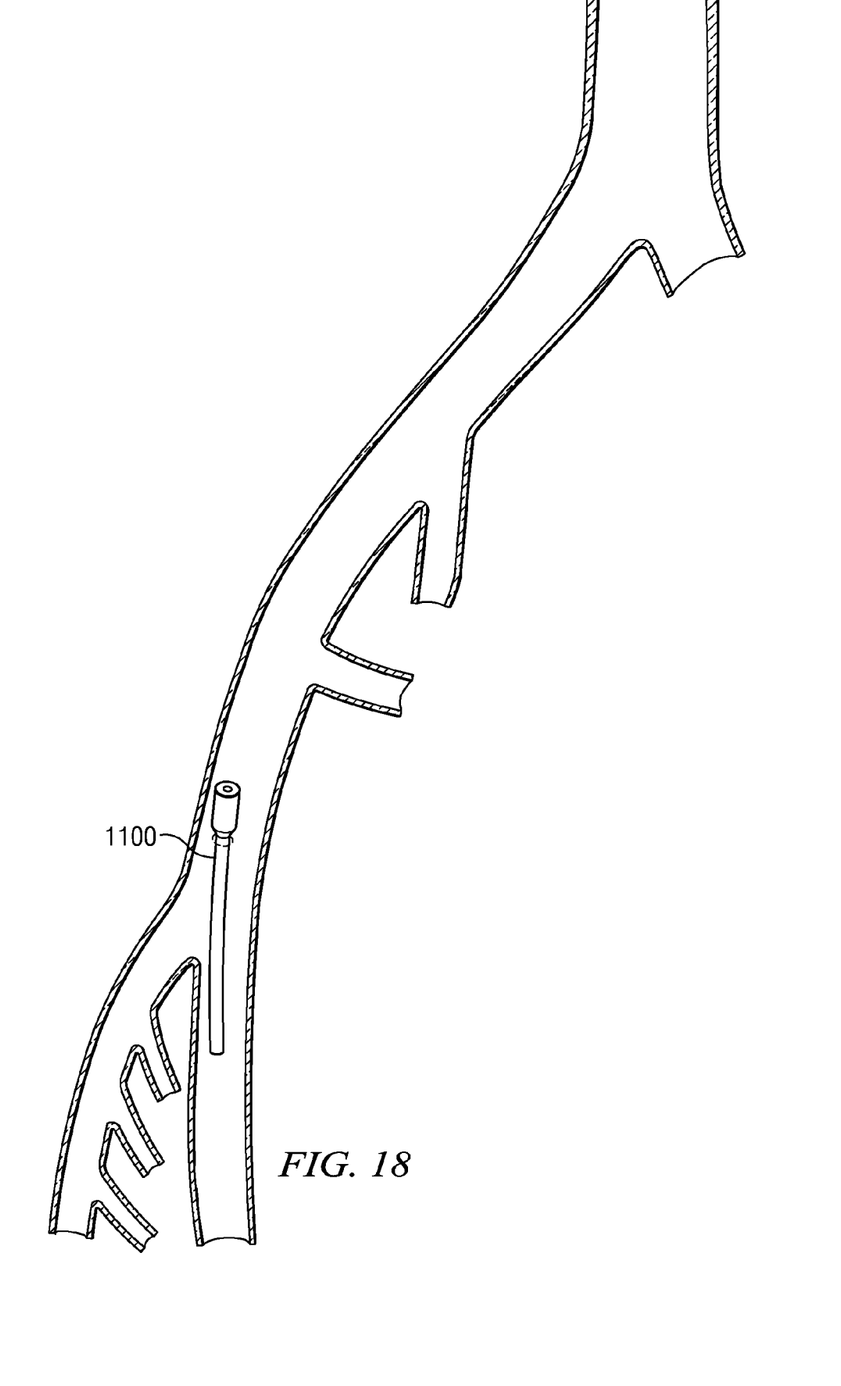
FIG. 18 is a view of the sheath with dilator and guide wire fully withdrawn.

Referring to FIGS. 11-18, a method of interventional reversal is shown. FIG. 11 shows dilator 1110 inserted over 0.035" guide wire 1120. In this particular example, the guide wire 1120 includes a soft hydrophilic tip and gradual stiffening such as a Terumo Glide wire. FIG. 12 shows the guide wire 1120 retracted into the bidirectional introducer assembly, this allows the dilator 1110 to recover an original shape. The introducer is pulled until only a curved portion emerges from sheath. The dashed line shows the direction of pull. The guide wire 1120 is mostly retracted. Referring to FIG. 13, arterial walls "trap" and preserve the original shape of the introducer tip. The sheath is withdrawn until a shaped tip of introducer is at arteriotomy level. Referring to FIG. 14, rotating the introducer as needed, the guide wire can be advanced into the superficial femoral artery. Referring to FIG. 15, the tip of the introducer is selectively pulled into the superficial femoral artery, rotating it as needed and the guide wire is advanced until the core is firmly in the artery. Referring to FIG. 16, the dilator is straightened and advanced. Referring to FIG. 17, the sheath is advanced over the straightened dilator. Referring to FIG. 18, the dilator and guide wire can be removed. This process can be inverted.

DEFINITIONS

The term substantially is intended to mean largely but not necessarily wholly that which is specified. The term approximately is intended to mean at least close to a given value (e.g., within 10% of). The term generally is intended to mean at least approaching a given state. The term coupled is intended to mean connected, although not necessarily directly, and not necessarily mechanically. The term proximate, as used herein, is intended to mean close, near adjacent and/or coincident; and includes spatial situations where specified functions and/or results (if any) can be carried out and/or achieved. The term distal, as used herein, is intended to mean far, away, spaced apart from and/or non-coincident, and includes spatial situation where specified functions and/or results (if any) can be carried out and/or achieved. The term deploying is intended to mean moving, activating, installing and/or operating.

The terms first or one, and the phrases at least a first or at least one, are intended to mean the singular or the plural unless it is clear from the intrinsic text of this document that it is meant otherwise. The terms second or another, and the phrases at least a second or at least another, are intended to mean the singular or the plural unless it is clear from the intrinsic text of this document that it is meant otherwise. Unless expressly stated to the contrary in the intrinsic text of this document, the term or is intended to mean an inclusive or and not an exclusive or. Specifically, a condition A or B is satisfied by any one of the following: A is true (or present) and B is false (or not present), A is false (or not present) and B is true (or present), and both A and B are true (or present). The terms a and/or an are employed for grammatical style and merely for convenience.

The term plurality is intended to mean two or more than two. The term any is intended to mean all applicable members of a set or at least a subset of all applicable members of the set. The phrase any range derivable therein is intended to mean any range within such corresponding numbers. The term means, when followed by the term "for" is intended to mean hardware, firmware and/or software for achieving a result. The term step, when followed by the term "for" is intended to mean a (sub)method, (sub)process and/or (sub)routine for achieving the recited result.

The terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. The terms "consisting" (consists, consisted) and/or "composing" (composes, composed) are intended to mean closed language that does not leave the recited method, apparatus or composition to the inclusion of procedures, structure(s) and/or ingredient(s) other than those recited except for ancillaries, adjuncts and/or impurities ordinarily associated therewith. The recital of the term "essentially" along with the term "consisting" (consists, consisted) and/or "composing" (composes, composed), is intended to mean modified close language that leaves the recited method, apparatus and/or composition open only for the inclusion of unspecified procedure(s), structure(s) and/or ingredient(s) which do not materially affect the basic novel characteristics of the recited method, apparatus and/or composition.

Unless otherwise defined, all technical and scientific terms used herein have the same meaning as commonly understood by one of ordinary skill in the art to which this invention belongs. In case of conflict, the present specification, including definitions, will control.

CONCLUSION

The described embodiments and examples are illustrative only and not intended to be limiting. Although embodiments of the invention can be implemented separately, embodiments of the invention may be integrated into the system(s) with which they are associated. All the embodiments of the invention disclosed herein can be made and used without undue experimentation in light of the disclosure. Although the best mode of the invention contemplated by the inventor(s) is disclosed, embodiments of the invention are not limited thereto. Embodiments of the invention are not limited by theoretical statements (if any) recited herein. The individual steps of embodiments of the invention need not be performed in the disclosed manner, or combined in the disclosed sequences, but may be performed in any and all manner and/or combined in any and all sequences. The individual components of embodiments of the invention need not be formed in the disclosed shapes, or combined in the disclosed configurations, but could be provided in any and all shapes, and/or combined in any and all configurations. The individual components need not be fabricated from the disclosed materials, but could be fabricated from any and all suitable materials. Homologous replacements may be substituted for the substances described herein. Agents which are both chemically and physiologically related may be substituted for the agents described herein where the same or similar results would be achieved.

Various substitutions, modifications, additions and/or rearrangements of the features of embodiments of the invention may be made without deviating from the spirit and/or scope of the underlying inventive concept. All the disclosed elements and features of each disclosed embodiment can be combined with, or substituted for, the disclosed elements and features of every other disclosed embodiment except where such elements or features are mutually exclusive. The spirit and/or scope of the underlying inventive concept as defined by the appended claims and their equivalents cover all such substitutions, modifications, additions and/or rearrangements.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

What is claimed is:

1. A bidirectional introducer, comprising a catheter including:
    a sheath; and
    a dilator located within and substantially coaxially with the sheath, the dilator having a distal end portion that includes a first section having a proximal first section end and a distal first section end, a second softer section having a proximal second section end and a distal second section end, a third reinforced section having a proximal third section end and a distal third section end, and a fourth section having a proximal fourth section end and a distal fourth section end, wherein a) the distal first section end is coupled to the proximal second section end, the distal second section end is coupled to the proximal third section end, and the distal third section end is coupled to the proximal fourth section end and b) i) at least a portion of the first section is characterized by a first rigidity and at least a portion of the second softer section is characterized by a second rigidity that is lower than the first rigidity, ii) at least a portion of the third reinforced section is characterized by a third rigidity that is higher than both the first rigidity and the second rigidity, and iii) at least a portion of the fourth section is characterized by a fourth rigidity that is lower than the third rigidity and higher than the second rigidity.

2. The bidirectional introducer of claim 1, further comprising a guide wire located within and substantially coaxially with the dilator, wherein the guide wire can be moved relative to the dilator to increase a radius of curvature characterized by the distal end portion.

3. The bidirectional introducer of claim 2, wherein the guide wire includes a soft hydrophilic tip and gradual stiffening.

4. The bidirectional introducer of claim 1, wherein the sheath includes a manifold for introduction of a fluid.

5. The bidirectional introducer of claim 1, wherein the distal end portion includes a fifth softer section having a proximal fifth section end and a distal fifth section end, wherein a) the distal fourth section end is coupled to the proximal fifth section end and b) at least a portion of the fifth softer section is characterized by a fifth rigidity that is lower than the first rigidity.

6. A kit of parts for assembly of a bidirectional introducer comprising a catheter including:
    a sheath;
    a dilator having a distal end portion that includes a first section having a proximal first section end and a distal first section end, a second softer section having a proximal second section end and a distal second section end, a third reinforced section having a proximal third section end and a distal third section end, and a fourth section having a proximal fourth section end and a distal fourth section end, wherein a) the distal first section end is coupled to the proximal second section end, the distal second section end is coupled to the proximal third section end, and the distal third section end is coupled to the proximal fourth section end and b) i) at least a portion of the first section is characterized by a first rigidity and at least a portion of the second softer section is characterized by a second rigidity that is lower than the first rigidity, ii) at least a portion of the third reinforced section is characterized by a third rigidity that is higher than both the first rigidity and the second rigidity, and iii) at least a portion of the fourth section is characterized by a fourth rigidity that is lower than the third rigidity and higher than the second rigidity; and
    a guide wire.

7. The kit of parts of claim 6, wherein the guide wire is located within and substantially coaxially with the dilator, wherein the guide wire can be moved relative to the dilator to increase a radius of curvature characterized by the distal end portion.

8. The kit of parts of claim 7, wherein the guide wire includes a soft hydrophilic tip and gradual stiffening.

9. The kit of parts of claim 6, wherein the sheath includes a manifold for introduction of a fluid.

10. The bidirectional introducer of claim 6, wherein the distal end portion includes a fifth softer section having a proximal fifth section end and a distal fifth section end, wherein a) the distal fourth section end is coupled to the proximal fifth section end and b) at least a portion of the fifth softer section is characterized by a fifth rigidity that is lower than the first rigidity.

11. A bidirectional introducer, comprising a catheter including:
    a sheath; and
    a dilator located within and substantially coaxially with the sheath, the dilator having a distal end portion that includes at first section having a proximal first section end and a distal first section end, a second softer section having a proximal second section end and a distal second section end and a third reinforced section having a proximal third section end and a distal third section end, wherein a) the distal first section end is coupled to the proximal second section end and the distal second section end is coupled to the proximal third section end and b) i) at least a portion of the first section is characterized by a first rigidity and at least a portion of the second softer section is characterized by a second rigidity that is lower than the first rigidity and ii) at least a portion of the third reinforced section is characterized by a third rigidity that is higher than both the first rigidity and the second rigidity, wherein the distal end portion includes a fourth section having a proximal fourth section end and a distal fourth section end, wherein a) the distal third section end is coupled to the proximal fourth section end and b) at least a portion of the fourth section is characterized by a fourth rigidity that is lower than the third rigidity and higher than the second rigidity, and further comprising a guide wire located within and substantially coaxially with the dilator, wherein the guide wire can be moved relative to the dilator to increase a radius of curvature characterized by the distal end portion.

12. The bidirectional introducer of claim 11, wherein the distal end portion includes a fifth softer section having a proximal fifth section end and a distal fifth section end, wherein a) the distal fourth section end is coupled to the proximal fifth section end and b) at least a portion of the fifth softer section is characterized by a fifth rigidity that is than the first rigidity.

* * * * *